(12) United States Patent
Myers et al.

(10) Patent No.: US 7,326,215 B2
(45) Date of Patent: Feb. 5, 2008

(54) CURVED SURGICAL TOOL DRIVER

(75) Inventors: Reese K. Myers, Warsaw, IN (US);
Paul E. Salyer, Warsaw, IN (US);
Brian C. Mendenhall, Claypool, IN (US)

(73) Assignee: Symmetry Medical, Inc., Warsaw, IN (US)

( * ) Notice: Subject to any disclaimer, the term of this patent is extended or adjusted under 35 U.S.C. 154(b) by 819 days.

(21) Appl. No.: 10/284,003

(22) Filed: Oct. 30, 2002

(65) Prior Publication Data

US 2004/0087958 A1 May 6, 2004

(51) Int. Cl.
*A61B 17/00* (2006.01)
*A61B 17/58* (2006.01)

(52) U.S. Cl. .......................................... 606/80; 606/96

(58) Field of Classification Search ................ 408/127, 408/239 R; 81/177.6, 177.5, 177.75, 177.2; 606/80, 96, 81; 279/93, 145; 403/349
See application file for complete search history.

(56) References Cited

U.S. PATENT DOCUMENTS

| | | | | |
|---|---|---|---|---|
| 1,409,554 | A | * | 3/1922 | Kitterman .................. 81/57.28 |
| 2,958,349 | A | * | 11/1960 | McNutt ........................ 408/67 |
| 4,034,574 | A | * | 7/1977 | Kuder ........................ 464/106 |
| 4,067,340 | A | | 1/1978 | Le Noir ....................... 128/305 |
| 4,075,913 | A | * | 2/1978 | Tye ............................ 81/177.75 |
| 4,645,388 | A | * | 2/1987 | Abrahamsen ................ 408/127 |
| 4,646,738 | A | * | 3/1987 | Trott ........................... 606/170 |
| 4,706,659 | A | | 11/1987 | Matthews et al. ............. 128/92 |
| 5,002,546 | A | | 3/1991 | Romano ....................... 606/80 |
| 5,387,218 | A | | 2/1995 | Meswania ..................... 606/80 |
| 5,395,188 | A | * | 3/1995 | Bailey et al. ................ 408/127 |
| 5,437,630 | A | | 8/1995 | Daniel et al. .................. 604/22 |
| 5,527,316 | A | | 6/1996 | Stone et al. .................... 606/80 |
| 5,690,545 | A | * | 11/1997 | Clowers et al. ............. 451/359 |
| 5,690,660 | A | | 11/1997 | Kauker et al. ............... 606/180 |
| 5,902,107 | A | * | 5/1999 | Lowell ......................... 433/130 |
| 5,957,925 | A | | 9/1999 | Cook et al. .................... 606/87 |
| 6,358,251 | B1 | | 3/2002 | Mirza ............................ 606/79 |
| 6,475,221 | B1 | * | 11/2002 | White et al. ................... 606/80 |
| 2003/0229356 | A1 | * | 12/2003 | Dye ............................ 606/99 |
| 2005/0216022 | A1 | | 9/2005 | Lechot et al. ................. 606/81 |
| 2005/0222572 | A1 | | 10/2005 | Chana ........................... 606/81 |

FOREIGN PATENT DOCUMENTS

| | | | | |
|---|---|---|---|---|
| EP | 1149562 A2 | | 10/2001 | |
| WO | WO03092513 | * | 4/2003 | ............. 606/80 |
| WO | WO 03/065906 A2 | * | 8/2003 | |
| WO | WO03092513 | * | 11/2003 | ............. 606/80 |

* cited by examiner

*Primary Examiner*—Pedro Philogene
(74) *Attorney, Agent, or Firm*—Taylor & Aust, P.C.

(57) ABSTRACT

A surgical tool driver has a driven end connectable to a rotary drive source and a driving end connectable to a surgical tool. A shaft assembly there between includes a hollow outer shaft and a flexible drive shaft for transmitting rotary power from the driven end to the driving end. The shaft assemble is curved for bypassing anatomical features in a patient.

18 Claims, 2 Drawing Sheets

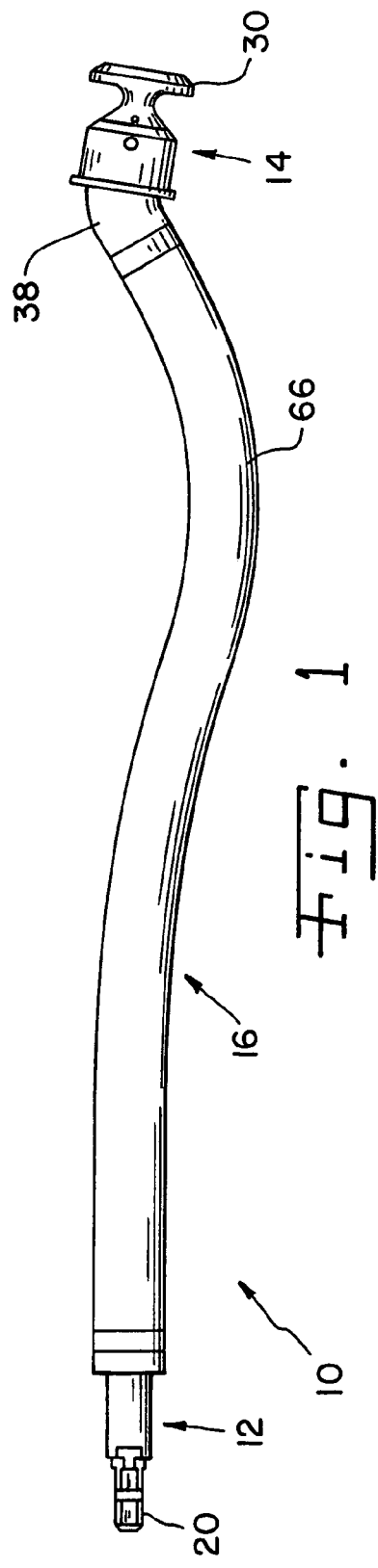
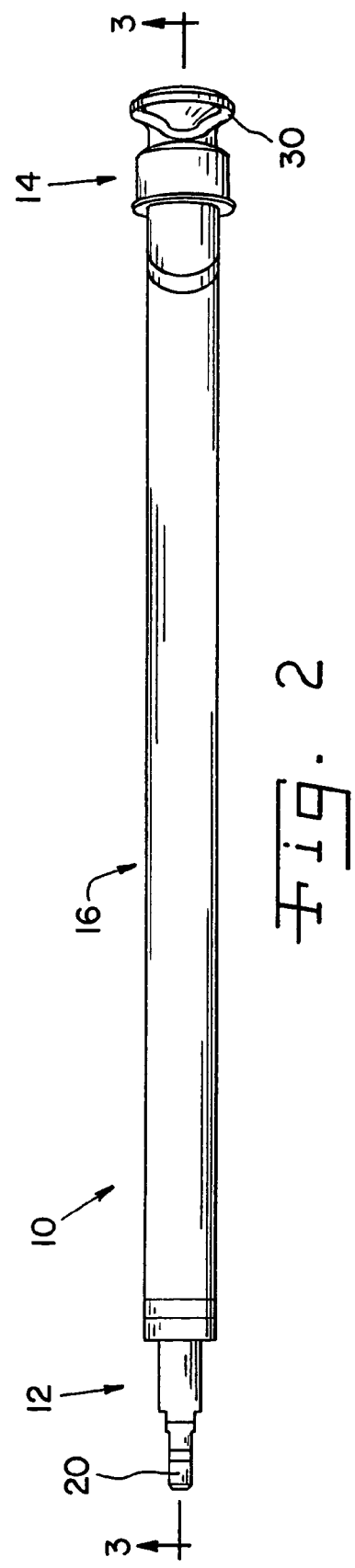

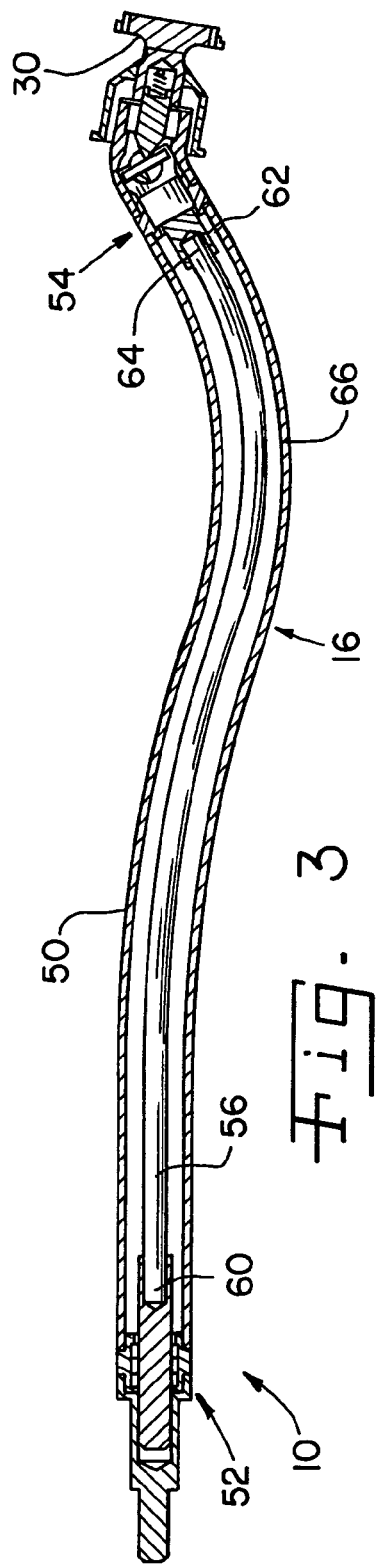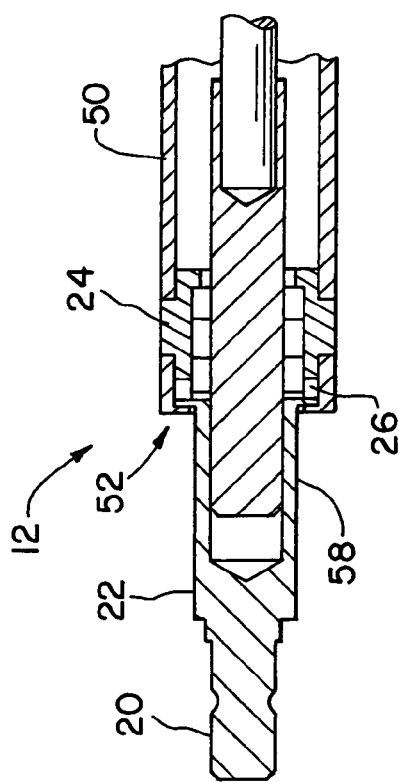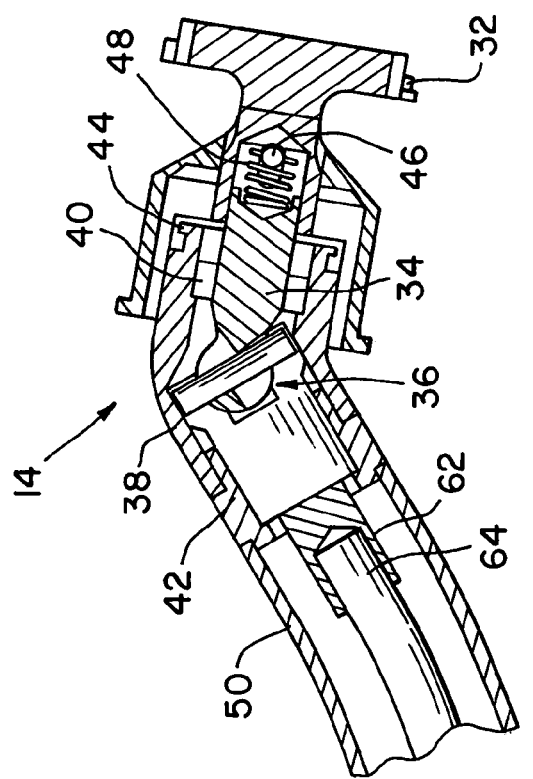

CURVED SURGICAL TOOL DRIVER

BACKGROUND OF THE INVENTION

1. Field of the Invention

The present invention pertains generally to surgical instruments and, more particularly, to surgical instruments such as surgical tool drivers particularly suited for use in minimal invasive surgical procedures.

2. Description of the Related Art

Early techniques for performing major orthopedic surgical procedures, such as joint replacements or reconstructions, included making large incisions and exposing the entire joint. Even with a successful surgery, the trauma to the patient is significant from open surgical procedures. As a result, rehabilitation periods are long and require dedication from the patient over an extended difficult time period to ensure the best possible result. Even with a skilled surgeon and a patient committed to a rehabilitation program, it is not always possible to achieve the desired results due in part to the surgical damage to areas surrounding the joint and the extensive scaring that can result.

In an effort to reduce trauma caused by open surgical procedures, it is desirable to reduce the size of incisions. Some procedures, such as many procedures performed on knees, now are routinely performed arthroscopically. Small incisions are made at discrete locations around the knee, and surgical tools are inserted through the incisions for performing the required procedures. Inspection of the joint, and observation of the procedure are achieved remotely, using fiber optics inserted through one of the incisions to illuminate the site and display a picture thereof on a view screen.

Procedures for knees and some other joints are readily adaptable to arthroscopic performance, using essentially straight, inline surgical tools. However, procedures for some other joints, such as hips, are not as easily adapted to minimally invasive surgical procedures. Because of surrounding hard and soft tissue structures, it is difficult to position properly inline surgical tools through incisions spaced about the joint. For example, to perform total hip arthroplasty, an acetabulum is prepared by forming a depression to receive an acetabular cup. The depression is formed with a cup-shaped reamer driven by a rotary driver. Known reamer drivers have included drive shafts of steel or other metals, requiring a straight approach to the site at which the depression will be formed. Because of obscuring anatomical features, it is difficult to use known acetabular reamers during a minimal invasive hip arthroplasty. Proper alignment of the tool is hindered by the intervening anatomical structures.

As a consequence, many common hip procedures, such as total hip replacements, are routinely performed through large incisions, in open procedures, exposing the entire joint, with the increased trauma caused thereby perceived as a necessary disadvantage.

What is needed in the art is a surgical tool driver that is more easily positioned through small surgical incisions, such as for reaming for an acetabular cup implant during minimally invasive procedures.

SUMMARY OF THE INVENTION

The present invention provides a surgical tool driver with a curved shaft facilitating proper positioning of working tools during minimally invasive surgical procedures, even when an access wound is created such that the target anatomy for machining is obscured by other anatomy.

The invention comprises, in one form thereof, a surgical tool driver with a hollow elongated outer shaft having a first end and a second end. The outer shaft has a fixed curved portion between the first end and the second end. The fixed curved portion is adapted and arranged along the outer shaft for bypassing anatomical structures in a patient between the first and second ends as the driver is positioned for use. A driven end attachment assembly at one the end of the outer shaft is adapted for attachment to a rotary drive source. A driving end attachment assembly at the other the end of the outer shaft is adapted for selectively engaging and disengaging a surgical tool. A flexible drive shaft is disposed in the outer shaft, with one end of the flexible drive shaft connected to the driven end attachment assembly, and the other end of the flexible drive shaft connected to the driving end attachment assembly.

The invention comprises, in another form thereof, a driver for an acetabular reamer with a hollow elongated outer shaft having a first end and a second end. The outer shaft has a fixed curved portion between the first end and the second end. The fixed curved portion is adapted and arranged along the outer shaft for bypassing anatomical structures in a patient between the first and second ends as the driver is positioned for use. A driven end attachment assembly at one the end of the outer shaft is adapted for attachment to a rotary drive source. A driving end attachment assembly at the other the end of the outer shaft is adapted for selectively engaging and disengaging an acetabular reamer. A flexible drive shaft is disposed in the outer shaft, with one end of the flexible drive shaft connected to the driven end attachment assembly, and the other end of the flexible drive shaft connected to the driving end attachment assembly.

The invention comprises, in yet another form thereof, a method for surgically preparing a bone, having steps of providing a surgical tool driver with a driven end attachment assembling and a driving end attachment assembly, and a curved shaft assembly there between, the curved shaft assembly including a rigid hollow outer shaft and a flexible drive shaft in the outer shaft, the flexible drive shaft connected to the driven end attachment assembling and the driving end attachment assembly; providing a surgical tool for machining a surface of the bone; attaching the surgical tool to the driving end attachment assembly; connecting the driven end attachment assembly to a rotary drive source; inserting the surgical tool through a surgical wound; positioning the surgical tool against a bone surface while positioning the curved portion of the shaft assembly around intervening anatomy; and driving the tool to machine the bone surface.

An advantage of the present invention is providing a surgical tool driver suitable for use in minimally invasive surgical procedures.

Another advantage is of the present invention is providing a surgical tool driver that facilitates proper tool placement even with anatomical structures present between an incision through which the tool is inserted and the site at which the tool is targeted.

Yet another advantage is providing a surgical tool driver for minimally invasive surgical procedures that can be adapted for use with different types of driving sources and for different types of surgical tools.

BRIEF DESCRIPTION OF THE DRAWINGS

The above-mentioned and other features and advantages of this invention, and the manner of attaining them, will become more apparent and the invention will be better understood by reference to the following description of an embodiment of the invention, taken in conjunction with the accompanying drawings, wherein:

FIG. 1 is a elevational view a curved surgical tool driver of the present invention;

FIG. 2 is a top plan view of the curved surgical tool driver shown in FIG. 1;

FIG. 3 is a cross-sectional view of the curved surgical tool driver shown in FIGS. 1 and 2, taken along line 3-3 of FIG. 2;

FIG. 4 is an enlarged cross-sectional view of one end of the curved surgical tool driver; and FIG. 5 is an enlarged cross-sectional view of the end of the curved surgical tool driver opposite the end shown in FIG. 4.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, and more particularly to FIG. 1, there is shown a medical instrument in the nature of a surgical tool driver 10 of the present invention. Driver 10 is particularly suited for use in minimally invasive surgical procedures, such as total hip arthroplasty performed through small surgical incisions. Driver 10 generally includes a driven end attachment assembly 12, a driving end attachment assembly 14, and a shaft assembly 16 extending generally between driven end attachment assembly 12 and driving end attachment assembly 14.

Driven end attachment assembly 12 includes a drive coupling 20, by which tool driver 10 is coupled to a rotary drive source. Coupling 20 is an exposed portion of a short shaft 22 retained in a sleeve 24 connected to shaft assembly 16. A bearing or bearings 26 allow shaft 22 to rotate relative to sleeve 24. It should be understood that coupling 20 may be provided in a variety of different shapes, configurations, sizes and forms, to connect to different rotary drive sources (not shown).

Driving end attachment assembly 14 is adapted for selective attachment to and detachment from orthopedic devices or tools (not shown) such as an acetabular reamer (not shown). Driving end attachment assembly 14 includes an exposed fixture 30 rotatably mounted relative to shaft assembly 16, and may include various bayonet catches 32, clasps, threaded segments or the like for drivingly attaching a surgical tool thereto. Various different types of fixtures 30 can be used for connecting surgical tool driver 10 to different types and sizes of surgical tools (not shown).

Fixture 30 is drivingly connected to a short shaft 34 that is drivingly connected to a swivel drive 36, such as a universal joint. Swivel drive 36 is disposed rotatably in an elbow 38 at the end of shaft assembly 16. Various different types of swivel drives 36 are known to those skilled in the art. Bearings 40 and 42 are provided for securing driving end attachment assembly 14, and specifically shaft 34 thereof, relative to shaft assembly 16. Shaft 34 projects outwardly of a cap 44 on shaft assembly 16, and, in the exemplary embodiment, is secured releasably to fixture 30 by a dowel pin 46 and compression spring 48.

Shaft assembly 16 includes a hollow outer shaft 50 having a first end 52 connected to driven end attachment assembly 12, and a second end 54 connected to driving end attachment assembly 14. A flexible drive shaft 56 is connected at one end to shaft 22 of driven end attachment assembly 12, and at an opposite end to swivel drive 36 of driving end attachment assembly 14. To connect flexible drive shaft 56 to shaft 22 of driven end attachment assembly 12, shaft 22 can be provided with a hollow end 58. A first end 60 of flexible drive shaft 56 is secured in hollow end 58 by, for example, attachment such as crimping of hollow end 58, compression from a set screw (not shown) direct adherence from adhesives, solder or welding, combinations of these techniques, or the like.

From shaft 22, flexible drive shaft 56 extends through hollow outer shaft 50 to driving end attachment assembly 14. Flexible drive shaft 56 is connected to swivel drive 38 similarly to the connection to shaft 22. A receiver 62 from swivel drive 38 is adapted to receive a second end 64 of flexible drive shaft 56. Second end 64 is secured in receiver 62 by, for example, attachment such as crimping of receiver 62, compression from a set screw (not shown) direct adherence from adhesives, solder or welding, combinations of these techniques, or the like.

As shown most clearly in FIGS. 1 and 3, hollow outer shaft 50 has a curved portion 66 between driven end attachment assembly 12 and driving end attachment assembly 14. Driving end attachment assembly 14 and driven end attachment assembly 12, in the exemplarary embodiment are in substantial linear alignment, with curved portion 66 of outer shaft 50 leading into elbow 38, permitting proper alignment between driven end attachment assembly 12 and driving end attachment assembly 14, even as shaft assembly 16 is positioned around anatomical features of a patient being operated on.

Drive shaft 56 as shown is flexible through out its length; however, it should be understood that drive shaft 56 is required to be flexible only along lengths thereof extending through curved portion 66, and as necessary to feed drive shaft 56 into outer shaft 50. Along straight lengths of outer shaft 50, drive shaft 56 can be rigid. Flexibility in drive shaft 56 is required only to allow rotation thereof within curved portion 66, although the entire length of drive shaft 56 can be flexible, if so desired. Drive shaft 56 can be conventional wound-wire flexible shafting, with alternating layers wound in opposite directions. A protective sheath (not shown) can be provided thereon. Other types of flexible shafting also can be used. Spaced standoffs (not shown) and/or lubricant can be provided within outer shaft 50, to allow proper position of drive shaft 56 in outer shaft 50, and to reduce resistance to rotation of drive shaft 56 within outer shaft 50.

In the use of surgical tool driver 10, a surgical tool, such as an acetabular reamer (not shown) is attached to fixture 30, and drive coupling 20 is connected to a source of rotary power (not shown). Driving end attachment assembly 14 is inserted through a surgical incision made in the patient, and the surgical tool (not shown) is brought into position for machining the bone being prepared. The curved design of shaft assembly 16 allows driver 10 to be positioned around intervening anatomical structures between the surgical incision and the bone are to be machined. The intervening anatomical structures are positioned within the space defined by curved portion 66.

Curved portion 66 can be provided at different locations along the length of outer shaft 50, in different radii of curvature, and can have compound curvature, to facilitate the use of surgical tool driver 10 for different procedures and surgical approaches. While shown and described with driven end attachment assembly 12 in substantial linear alignment with driving end attachment assembly 14, an angular offset arrangement also can be used, as necessary.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A surgical tool driver, comprising:
   a hollow elongated outer shaft having a first end and a second end, said outer shaft having means for bypassing anatomical structures in a patient, including a fixed curved portion along said outer shaft for bypassing anatomical structures in a patient between said first and second ends as said driver is positioned for use;
   a driven end attachment assembly at one said end of said outer shaft, said driven end attachment assembly including means for attachment to a rotary drive source;
   a driving end attachment assembly at the other said end of said outer shaft, said driving end attachment assembly including means for selectively engaging and disengaging a surgical tool; and
   a flexible drive shaft disposed in said outer shaft, one end of said flexible drive shaft being connected to said driven end attachment assembly, and the other end of said flexible drive shaft being connected to said driving end attachment assembly.

2. A surgical tool driver, comprising:
   a hollow elongated outer shaft having a first end and a second end, said outer shaft having a fixed curved portion between said first end and said second end, said fixed curved portion adapted and arranged along said outer shaft for bypassing anatomical structures in a patient between said first and second ends as said driver is positioned for use;
   a driven end attachment assembly at one said end of said outer shaft, said driven end attachment assembly being adapted for attachment to a rotary drive source;
   a driving end attachment assembly at the other said end of said outer shaft, said driving end attachment assembly adapted for selectively engaging and disengaging a surgical tool;
   a flexible drive shaft disposed in said outer shaft, one end of said flexible drive shaft being connected to said driven end attachment assembly, and the other end of said flexible drive shaft being connected to said driving end attachment assembly; and
   said driving end attachment assembly including a universal joint drivingly connected to said flexible drive shaft.

3. The surgical tool driver of claim 2, said driven end attachment assembly and said driving end attachment assembly disposed in substantial linear alignment.

4. The surgical tool driver of claim 1, said driven end attachment assembly and said driving end attachment assembly disposed in substantial linear alignment.

5. The surgical tool driver of claim 1, said outer shaft having a collar, and said driven end attachment assembly including a shaft adapted for attachment to a drive source, said shaft journaled in bearings in said collar.

6. The surgical tool driver of claim 5, said shaft of said driven end attachment assembly and said driving end attachment assembly disposed in substantial linear alignment.

7. The surgical tool driver of claim 5, said shaft of said driven end attachment assembly having a hollow end, and said flexible drive shaft being secured in said hollow end.

8. A surgical tool driver, comprising:
   a hollow elongated outer shaft having a first end and a second end, said outer shaft having a fixed curved portion between said first end and said second end, said fixed curved portion adapted and arranged along said outer shaft for bypassing anatomical structures in a patient between said first and second ends as said driver is positioned for use;
   a driven end attachment assembly at one said end of said outer shaft, said driven end attachment assembly being adapted for attachment to a rotary drive source;
   a driving end attachment assembly at the other said end of said outer shaft, said driving end attachment assembly adapted for selectively engaging and disengaging a surgical tool;
   a flexible drive shaft disposed in said outer shaft, one end of said flexible drive shaft being connected to said driven end attachment assembly, and the other end of said flexible drive shaft being connected to said driving end attachment assembly;
   said outer shaft having a collar, and said driven end attachment assembly including a shaft adapted for attachment to a drive source, said shaft journaled in bearings in said collar; and
   said driving end attachment assembly including a universal joint drivingly connected to said flexible drive shaft.

9. The surgical tool driver of claim 8, said shaft of said driven end attachment assembly having a hollow end, and said flexible drive shaft being secured in said hollow end.

10. The surgical tool driver of claim 9, said shaft of said driven end attachment assembly and said driving end attachment assembly disposed in substantial linear alignment.

11. A driver for an acetabular reamer, comprising:
    a hollow elongated outer shaft having a first end and a second end, said outer shaft having means for bypassing anatomical structures in a patient, including a fixed curved portion along said outer shaft for bypassing anatomical structures in a patient between said first and second ends as said driver is positioned for use;
    a driven end attachment assembly at one said end of said outer shaft, said driven end attachment assembly including means for attachment to a rotary drive source;
    a driving end attachment assembly at the other said end of said outer shaft, said driving end attachment assembly including means for selectively engaging and disengaging an acetabular reamer; and
    a flexible drive shaft disposed in said outer shaft, one end of said flexible drive shaft being connected to said driven end attachment assembly, and the other end of said flexible drive shaft being connected to said driving end attachment assembly.

12. The driver of claim 11, said driven end attachment assembly and said driving end attachment assembly being in substantially linear alignment.

13. A driver, for an acetabular reamer, comprising:
    a hollow elongated outer shaft having a first end and a second end, said outer shaft having a fixed curved portion between said first end and said second end, said fixed curved portion adapted and arranged along said outer shaft for bypassing anatomical structures in a patient between said first and second ends as said driver is positioned for use;

a driven end attachment assembly at one said end of said outer shaft, said driven end attachment assembly being adapted for attachment to a rotary drive source;

a driving end attachment assembly at the other said end of said outer shaft, said driving end attachment assembly adapted for selectively engaging and disengaging an acetabular reamer;

a flexible drive shaft disposed in said outer shaft, one end of said flexible drive shaft being connected to said driven end attachment assembly, and the other end of said flexible drive shaft being connected to said driving end attachment assembly; and said driving end attachment assembly including a universal joint connected to said flexible drive shaft.

14. The driver of claim 13, said driven end attachment assembly including a shaft, and said outer shaft having a collar for rotatably receiving said shaft of said driven end attachment assembly.

15. The driver of claim 14, said shaft of said driven end attachment assembly having a hollow end, and said flexible drive shaft having an end thereof secured in said hollow end.

16. The driver of claim 15, said shaft of said driven end attachment assembly being in substantially linear alignment with said driving end attachment assembly.

17. The driver of claim 15, said driving end attachment assembly having a hollow receiver, and said flexible drive shaft having an end thereof secured in said hollow receiver.

18. An apparatus to practice a method for surgically preparing a bone, comprising:

means for providing a surgical tool driver with a driven end attachment assembling and a driving end attachment assembly, and a curved shaft assembly there between, said curved shaft assembly including a rigid hollow outer shaft and a flexible drive shaft in said outer shaft, said flexible drive shaft connected to said driven end attachment assembling and said driving end attachment assembly;

means for providing a surgical tool for machining a surface of the bone;

means for attaching the surgical tool to the driving end attachment assembly;

means for connecting the driven end attachment assembly to a rotary drive source;

means for inserting the surgical tool through a surgical wound;

means for positioning the surgical tool against a bone surface while positioning the curved portion of the shaft assembly around intervening anatomy; and means for driving the tool to machine the bone surface.

* * * * *